United States Patent [19]

Paul

[11] 4,243,041
[45] Jan. 6, 1981

[54] COLD-PACK GOGGLES

[76] Inventor: Malcolm D. Paul, 111 Via Undine, Newport Beach, Calif. 92663

[21] Appl. No.: 27,447

[22] Filed: Apr. 5, 1979

Related U.S. Application Data

[63] Continuation of Ser. No. 864,030, Dec. 23, 1977, abandoned, which is a continuation of Ser. No. 722,188, Sep. 10, 1976, abandoned.

[51] Int. Cl.³ .............................................. A61F 7/00
[52] U.S. Cl. ...................................... 128/402; 128/403
[58] Field of Search ............... 128/399, 402, 403, 380, 128/258

[56] References Cited

U.S. PATENT DOCUMENTS

| | | | |
|---|---|---|---|
| 614,108 | 11/1898 | Hommell | 128/402 X |
| 1,886,725 | 11/1932 | Pedersen | 128/402 |
| 2,024,491 | 12/1935 | Veysey | 128/163 |
| 2,101,628 | 12/1937 | Padelford | 150/2.3 |
| 2,582,345 | 1/1952 | Moeller | 2/446 |
| 2,607,919 | 8/1952 | Stegeman | 2/446 |
| 2,635,605 | 4/1953 | Becker | 128/380 |
| 3,195,539 | 7/1965 | Hyman | 128/256 |
| 3,339,206 | 9/1967 | Daley | 2/2 |
| 3,354,884 | 11/1967 | Rudo | 128/260 |
| 3,606,890 | 9/1971 | Gilbert | 128/400 |
| 3,736,769 | 6/1973 | Petersen | 128/402 |
| 3,762,419 | 10/1973 | Walters | 128/403 |
| 3,768,485 | 10/1973 | Linick | 128/402 |
| 3,804,087 | 4/1974 | Sarnoff | 128/163 |
| 3,815,610 | 6/1974 | Winther | 128/380 |
| 3,868,984 | 3/1975 | Jorgensen | 128/403 X |
| 3,889,684 | 6/1975 | Lebold | 128/163 |
| 3,900,035 | 8/1975 | Welch | 128/402 |
| 3,952,735 | 4/1976 | Wirtschafter et al. | 128/163 |

FOREIGN PATENT DOCUMENTS

| | | | |
|---|---|---|---|
| 1488442 | 6/1967 | France | 2/446 |
| 1167481 | 10/1969 | United Kingdom | 128/403 |

Primary Examiner—Robert W. Michell
Assistant Examiner—Arthur S. Rose
Attorney, Agent, or Firm—Knobbe, Martens, Olson, Hubbard & Bear

[57] ABSTRACT

This invention relates to a cold therapy pack for use particularly in the relief of pain, swelling, or other discomforts of patients involved in cosmetic surgery in the facial area such as, rhinoplasty and blepharoplasty. The appliance comprises a goggle shaped plastic pack filled with a hydrophilic gel having the property of maintaining its pliability in a frozen state. As easily attached nose pack is provided when necessary.

4 Claims, 5 Drawing Figures

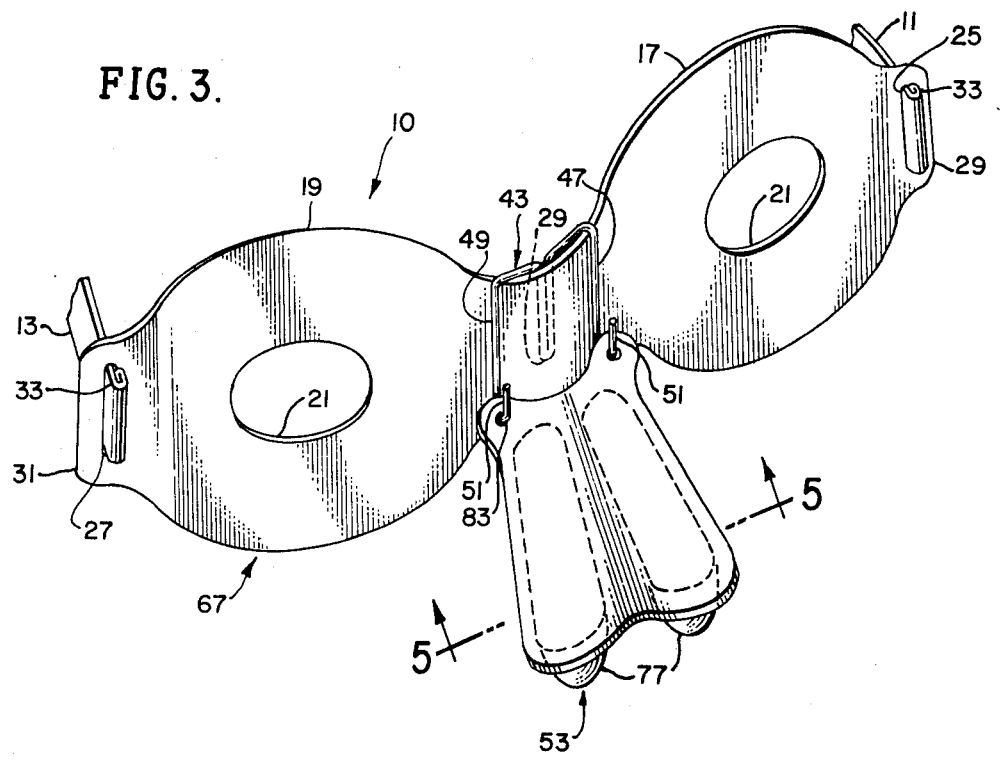
FIG. 3.
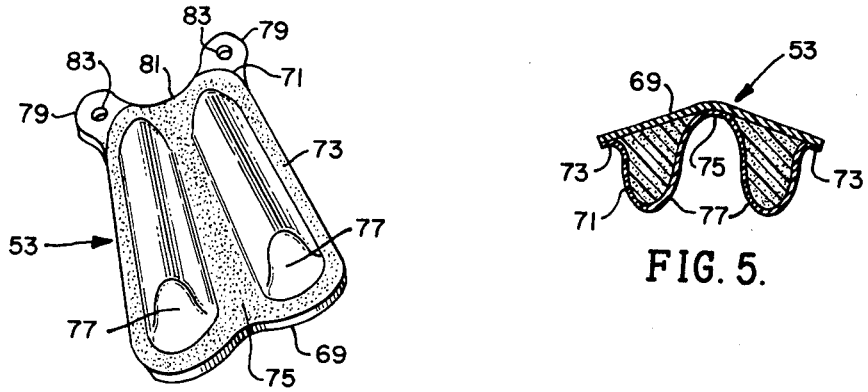
FIG. 4.
FIG. 5.

COLD-PACK GOGGLES

CROSS REFERENCE TO RELATED APPLICATIONS

This is a continuation of application Ser. No. 864,030, filed Dec. 23, 1977, abandoned, which was a continuation of application Ser. No. 722,188, filed Sept. 10, 1976, abandoned.

BACKGROUND OF THE INVENTION

It is conventional practice in post cosmetic surgery of the facial area to apply ice packs for relieving the discomfort of pain and swelling. Traditionally, these cold pack appliances comprised a water impermeable bag having a wide-mouth opening through which ice cubes could be inserted. For additional comfort said ice pack would be wrapped in a towel. When the ice cubes melted, the ice pack bag would be refilled. As can be envisioned, the task of changing the cold pack application was untidy and time consuming.

More recently, cooling devices comprising plastic bags filled with various hydrophilic gels have been introduced in the state of the art. When frozen, said devices retain their flexibility and can be conformed to the shape of the anatomy where required. However, in general, said coolant packs are large, bulky, and rectangular or square in configuration and introduce a weight factor which can prove to be extremely uncomfortable to the patient in a prone position. Said packs are usually difficult to keep in place and must be bandaged in position if the patient is permitted to rise from a reclining position. If used in the facial area, the eyesight of the patient is naturally impaired or completely blocked.

SUMMARY OF THE INVENTION

The present invention alleviates many of the disadvantages associated with the prior art. The preferred embodiment of the invention described herein comprises a goggle-shaped cold pack with adjustable straps for securing the pack tightly around the head of a patient. Eye openings are provided to allow unobstructed vision for the patient. The used pack can be quickly replaced from a reserve supply in a cold storage unit. The used cold pack goggles can be repeatedly refrozen and used without recharging. The cold pack elements can be washed when necessary or discarded. The Velcro straps are easily detached and can be used on the replacements.

BRIEF DESCRIPTION OF THE DRAWINGS

These and other advantages of the present invention are best understood through a reference to the drawings, in which:

FIG. 3 is a perspective view of the cold-pack goggles as viewed from the front, showing the nosebridge clip in place and the supplementary nose pack attached thereon;

FIG. 4 is a perspective view of the nose pack as viewed from the underside showing the projecting gel sacs; and FIG. 5 is a sectional view of the nose pack taken along lines 5—5 of FIG. 3.

DETAILED DESCRIPTION OF THE PREFERRED EMBODIMENT

Figure 1:
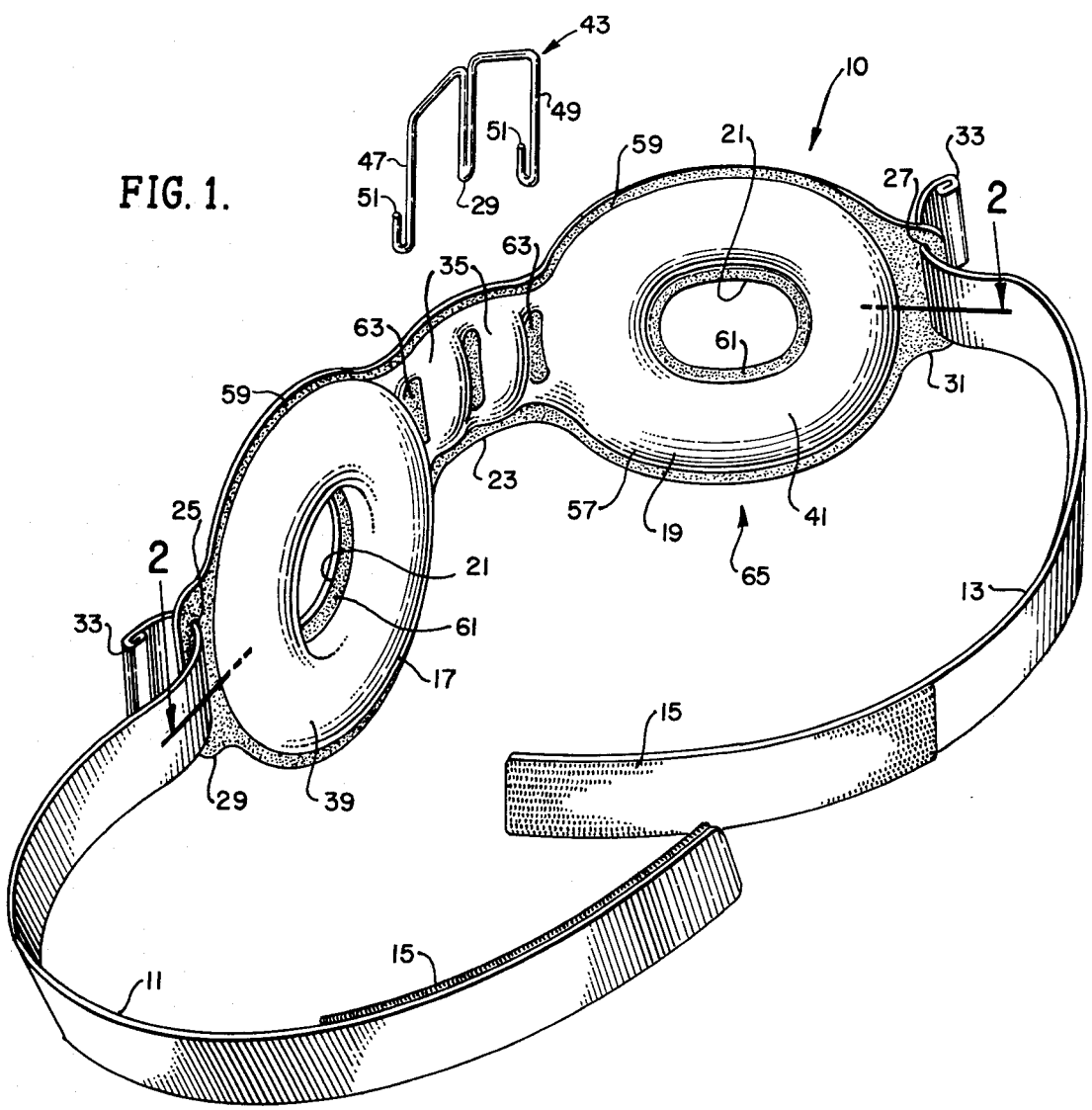
FIG. 1 is a perspective view of the cold-pack goggles as viewed from the inner side and showing the nosebridge clip detached and the nose pack removed.

Referring initially to FIG. 1, a cold therapy pack 10 is shown with its adjustable attachment means comprising detachable straps 11 and 13 having Velcro strips 15 cemented at the extremities of each strap. The pack 10 is shaped generally in the configuration of goggles having toroidal eyepieces 17 and 19 with eyeholes 21 joined together with a nosebridge 23. The straps 11, 13 are slidably attached to the pack 10 through elongate slots 25 and 27 in tabs 29, 31, respectively of the pack 10. The ends of straps 11, 13 are rolled and cemented at 33 preventing slippage through slots 25, 27. Each toroidal eyepiece 17 and 19 as well as two elongate sacs or compartments 35 in the nosebridge 23 is filled with a hydrophilic gel 37 as best shown in sectional view, FIG. 2. One such gel produced by the Medical Products Division of the 3M Company is marketed under the trade name CRYOGEL. Said hydrophilic gel 37 or any other gel substance which retains its pliable and flexible characteristic when maintained for prolonged periods in a water freezing temperature is used as the cold preservative material for the therapy pack 10. The toroidal eyepice compartments 39, 41 and nosebridge compartments 35 filled with said pliable gel 37 enable the cold therapy pack 10 to conform to the cavities around the eye sockets and the nose.

Figure 2:
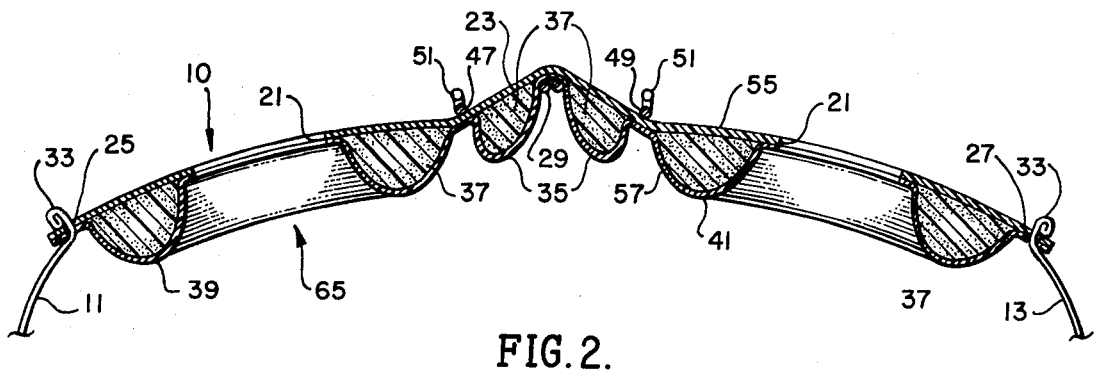
FIG. 2 is a sectional view of the cold-pack goggles taken along lines 2—2 of FIG. 1.

A three-prong wire clip 43 is slipped across the nosebridge 23 to maintain an arch in said bridge 23 (as best shown in FIG. 2) when the straps 11 and 13 are secured tightly around the head of the patient. The clip 43 is formed from a singular piece of wire into two inverted U-shapes with adjoining legs attached at 29. The outboard legs 47, 49 have their lower extremities turned upward into hooks 51, to permit smooth engagement over the bridge 23 and provide a means for attaching nose pack 53 shown in FIGS. 3 and 4.

Referring now specifically to FIG. 2, the basic construction of the cold therapy pack 10 comprises a thicker exterior layer of plastic material 55 whereon a thinner, more pliable sheeting of plastic 57 is heat sealed around the outer periphery 59 of the pack 10 and the inner periphery 61 of eyeholes 21 in each of the eyepieces 17 and 19. Three elongated heat seal spots 63 in the nosebridge 23 form gel compartments or sacs 35. The gel 37 is inserted under pressure into the pack 10 at either end through an unsealed gel inlet port (not shown) until the compartments around the eyepieces 17, 19 and the nosebridge compartments 35 are filled to a consistency permitting flexible manipulation of the pack 10 across the eyes and nose of a patient. The gel inlet port is heat sealed to completely encase the gel 37 within the impermeable plastic pack 10. Because the inner plastic sheeting 57 is more flexible than the outer plastic layer 55, the backside 65 of the pack 10 expands to accept the gel filler 37 thus forming contoured pockets which will fit closely across the features of the patient. The thicker ply of plastic 55 on the exterior of the pack 10 prevents cold transfer in that direction, thus making the pack 10 more effective in heat absorbtion at the swollen areas of the facial features.

Referring now specifically to FIGS. 3, 4 and 5, the exterior side 67 of the pack 10 is shown with the nose pack 53 attached to the clip 43. The nose pack 53 comprises an exterior layer 69 which is as thick as the exterior layer 55 of the pack 10 and an inner sheeting of plastic 71 which is heat sealed to the exterior sheet 69 around the periphery 73 and through the center 75 to form two gel compartments 77. The gel compartments 77 are of such size as to conform closely to the shape of the patient's nose on either side. The nose pack 53 has two ears 79 projecting from the upper edge 81 of its basic configuration. Holes 83 are provided in the ears 79 to enable the easy attachment of said pack 53 to the hooks 51 of the clip 43.

Although the basic configuration of the cold therapy pack 10 as described in the above preferred embodiment would be adaptable to most adult patients involved in cosmetic surgery such as rhinoplasty and blepharoplasty, a smaller configuration of reduced dimension can be manufactured for children undergoing such operations.

What is claimed is:

1. A cold therapy pack comprising:
   goggle-shaped eyepieces joined together by a nose bridge, said eyepieces comprising two layers of thermoplastic sheets heat sealed around their periphery to form a hydrophilic gel compartment between said sheets;
   a separate nose pack comprising a plurality of hydrophilic gel compartments and means for attaching same; and
   detachable Velcro straps for securing said pack tightly around the head of a patient.

2. A cold therapy pack comprising:
   goggle-shaped eyepieces joined together by a nose bridge, said eyepieces comprising two layers of thermoplastic sheets heat sealed around their periphery to form a hydrophilic gel compartment between their sheets;
   means for maintaining an arch in said nose bridge;
   means for securing said pack across the eyes of a patient; and
   a separate nose pack and means for attaching said nose pack to said eyepieces, said separate nose pack comprises two layers of thermoplastic sheets, heat sealed around the periphery and its vertical axis to form self-contained hydrophilic gel sacs on both sides of the central vertical axis and having projecting ears at the upper corners of its configuration.

3. A cold therapy pack as defined in claim 2 wherein the thermoplastic sheets comprising said separate nose pack are a thinner inner layer heat sealed to a thicker exterior layer.

4. A cold therapy pack comprising:
   goggle-shaped eyepieces joined together by a nose bridge, said eyepieces comprising two layers of thermoplastic sheets heat sealed around their periphery to form a hydrophilic gel compartment between said sheets;
   means for maintaining an arch in said nose bridge comprising a three-prong wire clip which forms an arch to said nose bridge when slipped in place across said bridge;
   means for securing said pack across the eyes of a patient; and
   a separate nose pack, said three-prong wire clip having hooks on the extremities of the outboard legs for attaching said separate nose pack to said eyepieces.

* * * * *